United States Patent [19]
Gross

[11] Patent Number: 5,549,584
[45] Date of Patent: Aug. 27, 1996

[54] APPARATUS FOR REMOVING FLUID FROM A WOUND

[75] Inventor: James R. Gross, Wareham, Mass.

[73] Assignee: The Kendall Company, Mansfield, Mass.

[21] Appl. No.: 194,976

[22] Filed: Feb. 14, 1994

[51] Int. Cl.[6] ........................................ A61M 1/00
[52] U.S. Cl. ........................ 604/313; 604/316; 604/319; 604/355
[58] Field of Search .................... 604/118, 119, 604/305, 313, 317, 73–75, 324, 319–321, 73, 289, 290, 315, 316, 183, 355; 602/14, 48, 58; 128/765, 767

[56] References Cited

U.S. PATENT DOCUMENTS

| | | | |
|---|---|---|---|
| 1,066,934 | 7/1913 | Manney | 604/355 |
| 1,228,451 | 6/1917 | Latta | 604/316 |
| 2,195,771 | 4/1940 | Estler | 604/355 |
| 2,606,555 | 8/1952 | Solomon | 604/326 |
| 3,567,675 | 3/1971 | Harvey | 604/355 |
| 4,051,852 | 10/1977 | Villari | 604/183 |
| 4,250,882 | 2/1981 | Adair | 604/355 |
| 4,457,759 | 7/1984 | Norton | 604/324 |
| 4,512,771 | 4/1985 | Norton | 604/324 |
| 4,551,141 | 11/1985 | McNeil | 604/319 |
| 4,795,435 | 1/1989 | Steer | 604/332 |
| 4,838,855 | 6/1989 | Lynn | 604/49 |
| 4,917,112 | 4/1990 | Kalt | 602/58 |
| 5,019,059 | 5/1991 | Goldberg et al. | 604/317 |
| 5,152,757 | 10/1992 | Eriksson | 604/305 |
| 5,244,457 | 9/1993 | Karami et al. | 602/55 |
| 5,437,651 | 8/1995 | Todd et al. | 604/313 |

FOREIGN PATENT DOCUMENTS

| | | | |
|---|---|---|---|
| 2809828 | 9/1978 | Germany | 604/289 |
| 0641061 | 8/1950 | United Kingdom | 604/289 |
| 2245833 | 1/1992 | United Kingdom | 604/73 |

*Primary Examiner*—John G. Weiss
*Assistant Examiner*—Mark O. Polutta
*Attorney, Agent, or Firm*—David J. Koris

[57] ABSTRACT

The invention features methods and apparatuses for evacuation of exudate from wounds. The apparatuses include a suctioning means having an inlet port and an outlet port, and a wound cover in fluid communication with the suctioning means via the inlet port. The wound cover is adapted to fit in fluid communication with a wound dressing for application to a wound site. The suctioning means is operative to remove exudate from a wound dressing in association with the wound cover and covering a wound site.

4 Claims, 3 Drawing Sheets

5,549,584

APPARATUS FOR REMOVING FLUID FROM A WOUND

FIELD OF THE INVENTION

The invention relates in general to apparatuses and methods for evacuating body fluids, in particular for evacuating exudate from a wound.

BACKGROUND OF THE INVENTION

It is desirable in medical procedures directed to the healing of wounds to remove fluid from the wound without contaminating the wound. This has been achieved using various wound dressings as absorbent agents to absorb fluid away from the wound.

One object of the invention is to promote wound healing by actively removing exudate from a wound without contamination. It is also an object of the invention to provide apparatuses and methods for removal of excessive wound exudate, while at the same time maintaining a moist environment for the wound to promote healing and prevent scab formation. Yet another object of the invention is to provide a system which is capable of removing various amounts of exudate from a wound, that is, which can accommodate variation in rate of exudate production by a wound.

SUMMARY OF THE INVENTION

The invention features an apparatus for evacuation of exudate from wounds, comprising a suctioning means having an inlet port and an outlet port, and a wound cover in fluid communication with the suctioning means via the inlet port, the wound cover being adapted to fit in fluid communication with a wound dressing for application to a wound site, wherein the suctioning means is operative to remove exudate from a wound dressing in communication with the wound cover and covering a wound site. As used herein, "exudate" refers to any fluid output from a wound, e.g., blood, serum, and/or pus, etc.

The apparatus may also include a vented wound dressing fitted so as to be in fluid communication with the wound cover when the dressing contains fluid, the wound dressing comprising a layer of absorbent material adjacent the wound cover and a wound surface layer of material, a portion of which includes an adhesive coating for adherence to the skin; the wound surface layer of material may include adhesive coating at the periphery of the wound dressing. The wound dressing is referred to herein as "vented" in that fluid may traverse the dressing layers, i.e., flow into the dressing at the wound surface layer, and flow out of the dressing at the surface distal the wound surface layer.

The invention also includes an apparatus for evacuation of exudate from wounds, comprising the suctioning means and wound cover described above, and also including a vented wound dressing comprising a thin conformable sheet material at least a portion of the surface area of which is intended for placement as a dressing over a wound, which portion carries a pressure-sensitive adhesive coating on one surface thereof for adhering the dressing to skin, the coating being applied to provide repeating areas of the sheet material containing no adhesive, at least a portion of the repeating areas of no adhesive having slits extending through the thickness thereof to permit transfer or wound fluids through the sheet material unimpeded by presence of adhesive material which can clog the slits and thereby inhibit fluid transfer therethrough.

As used herein, the wound cover is adapted to fit in fluid communication with a wound dressing by being sized and shaped to lie over the dressing as applied to a wound. Thus, the wound cover may completely or partially cover the dressing; where the cover completely covers the dressing, it will include sides of a depth corresponding to the thickness of the dressing.

Preferably, the suctioning means is compressible and expandable, e.g., operative like a bellows. The apparatus may also include a collection bag in fluid communication with the suctioning means via the outlet port. Inclusion of the collection bag allows for operation of an essentially closed system, and thus avoids contamination from microorganisms. A closed, uncontaminated system may also be maintained if the inlet port is fitted with a one-way inlet valve and the outlet port is fitted with a one-way outlet valve such that no air or fluid can flow in the direction of the wound.

The invention also includes methods of continuously or intermittently removing exudate from a wound. The methods include providing a wound dressing in operative combination with an apparatus for evacuation of exudate from wounds, the apparatus comprising a suctioning means having an inlet port and an outlet port, and a wound cover in fluid communication with the suctioning means via the inlet port, the wound cover being adapted to fit in fluid communication with a wound dressing for application to a wound site. The wound dressing in combination with the apparatus is applied to a wound for a time sufficient to allow exudate from the wound to leach into the wound dressing. The leached exudate is then removed from the wound dressing by operation of the suctioning means.

Another method of the invention includes a method of removing exudate from a wound by providing an apparatus comprising the suctioning means and wound cover containing the vented wound dressing, all as described above, and applying the wound dressing to a wound for a time sufficient to allow exudate from the wound to leach into the wound dressing. The leached exudate is then removed from the wound dressing by operation of the suctioning means.

The inventive methods may also include the steps of allowing additional exudate draining from the wound to leach into the wound dressing, and removing the additional leached exudate from the wound dressing using the suctioning means.

Preferably, in the applying step, the suctioning means of the apparatus is compressible and expandable, and the removing step comprises allowing the suctioning means in its compressed form to expand.

Also within methods of the invention is a method of removing fluid from a wound comprising the steps of positioning the wound cover of the apparatus which includes a suctioning means, and a wound cover in fluid communication with the suctioning means, the wound cover being adapted to fit with a wound dressing for application to a wound site, as described above, over a wound dressing at a wound site; and removing exudate from the wound by operation of the suctioning means.

As with the other methods, it is preferred that the suctioning means of the apparatus be compressible and expandable, and the removing step include allowing the suctioning means in its compressed form to expand.

The apparatuses and methods of the invention allow for easy removal of fluid from a wound while maintaining sterile conditions and keeping the wound in a moist state. The apparatuses may be manually operated or automated, thus providing for continuous or intermittent removal of wound exudate. The apparatuses are of simplified design and low cost to manufacture.

Further features will become more fully apparent in the following description of the embodiments of this invention and from the appended claims.

DETAILED DESCRIPTION OF THE INVENTION

The invention facilitates removal of wound exudate using a manual or automated fluid removing apparatus in combination with a vented wound dressing. The preferred vented wound dressing includes an adhesive layer for skin-adhesion.

It is most desirable, according to the invention, to provide a suctioning apparatus which includes an adhesive wound dressing designed so as to maintain a moist environment to promote healing while avoiding scab formation, and at the same time to permit removal of excessive wound fluid absorbed therethrough. The apparatuses described herein are useful for removing exudate from different wound types, particularly those wounds in which the rate of exudate production varies during healing. When produced in excess, wound exudate may cause a pressure build-up beneath the dressing and thus undermine the adhesive seal of the dressing to the skin, thereby increasing the possibility of the wound being contacted with ambient contaminants. Removal of wound exudate from a wound site promotes wound healing. Thus, where a wound produces greater amounts of exudate, the exudate may be removed according to the invention without drying the wound surface. Conversely, when the wound produces a smaller amount of exudate, only a small amount will be removed according to the invention, thus maintaining the wound in a moist state.

Figure 1:
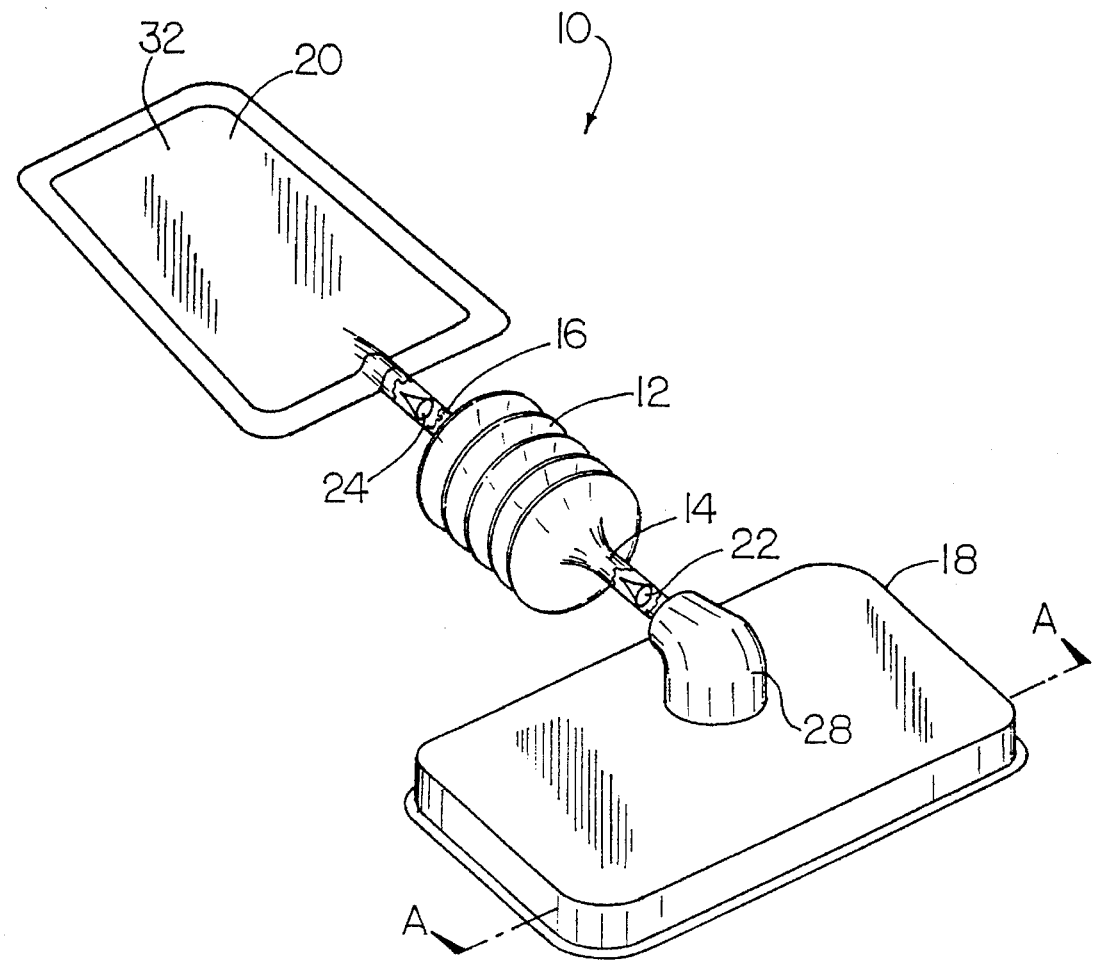
FIG. 1 is an elevational perspective view of the apparatus of the invention.

Turning to FIG. 1, an apparatus for collecting body fluids 10 according to the invention is illustrated, including a compressible and expandable suctioning means, e.g., a resilient bellows 12, having an inlet port 14 and an outlet port 16. Bellows 12 is attached to and in fluid communication with wound cover 18 via inlet port 14. Bellows 12 is also attached to and in fluid communication with collection bag 20 via outlet port 16. Bellows 12 serves as both the suctioning means of the invention as well as a pressure source. Bellows 12 may be made of polyethylene, or it may be made of other impervious resilient materials such as polypropylene. Suctioning may be accomplished using any sort of reservoir capable of producing sufficient negative pressure, when evacuated, to draw fluid from a wound site. Bellows 12 may have a liquid capacity in its normal extended state of about 150 cc.

Inlet ports 14 and 16 each include a one-way valve 22, 24, respectively. The one-way valve may be a gross reflux valve positioned between the bellows and either the wound cover or the collection bag. Any gross reflux valve may be used, e.g., a duckbill valve or another conventional one-way valve, such as ball,check and diaphragm valves, as long as the valve prevents fluid reflux and does not interfere with operation of the bellows.

Collection bag 20 may be a clear, flexible polyethylene bag although other impervious containers (flexible or rigid) may be used. The size of the collection bag, although a matter of choice, will typically be large enough to contain 500, 1000, or 2000 cc. of fluid.

Collection bag 20 may also include a vent 32 to permit air within the bag to escape as the bag becomes filled with liquid during wound drainage. The vent thus permits gases which may be drawn into the system from the wound site by way of wound cover 18 to escape.

Figure 2:
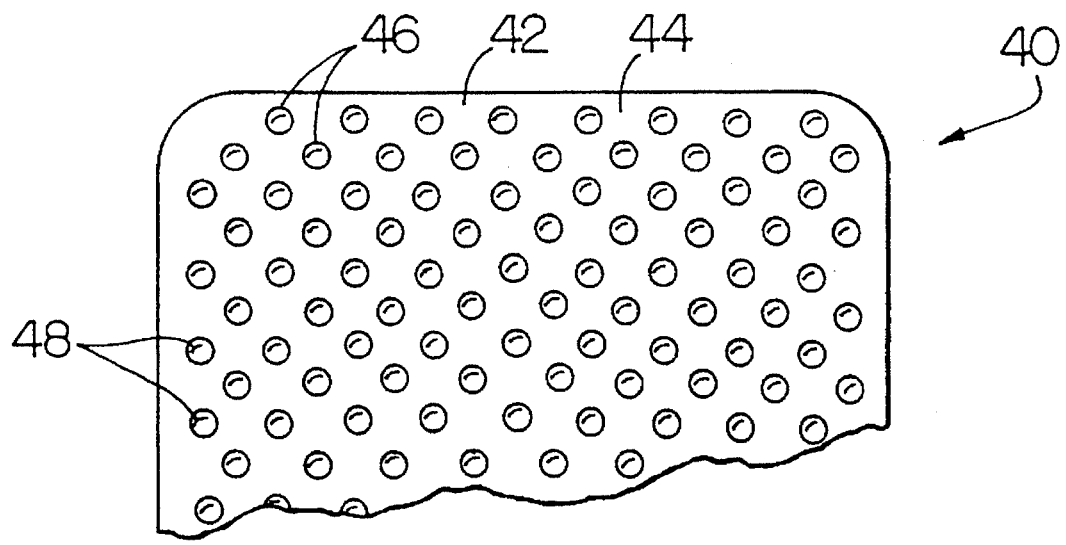
FIG. 2 is a plan view of the adhesive-bearing surface of a wound dressing useful according to the invention.
Figure 3:
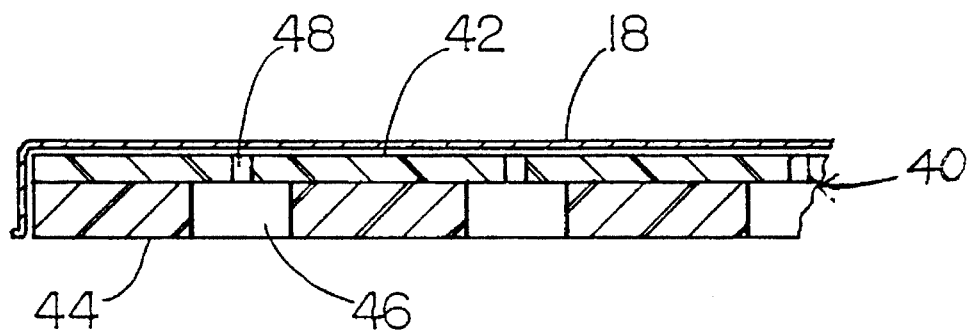
FIG. 3 is a partial sectional view taken along lines A—A of FIG. 1.

Wound cover 18 of the apparatus of the invention also includes an evacuation port 28, and a wound dressing 40 (as shown from its underside in FIG. 2 and in side-view in FIG. 3). The wound cover 18 is made of a semi-flexible, liquid-impervious material such as polypropylene, and is shaped so as to fit over the wound dressing, or a portion thereof, and to cover the wound, or a portion thereof. The wound dressing need not be attached to the underside or edges of the wound cover, but may simply be the same size as or slightly smaller than the wound cover, such that it fits easily within the wound cover. Evacuation port 28 is also made of a liquid-impervious material and connects wound cover 18 to inlet port 14.

Any vented wound dressing may be used in the fluid evacuation apparatus according to the invention. One especially preferred wound dressing is that described in co-pending application U.S. Ser. No. 07/738,983, now abandoned, assigned to the same assignee and hereby incorporated by reference. This application discloses a vented wound dressing, which is particularly preferred because it allows for adherence to the wound, while also promoting removal of exudate from the wound. Portions of the wound surface of this wound dressing contain an adhesive which adheres to the wound, while the remaining portions are non-adhesive and are slit so as to promote fluid transfer away from the wound site and into the non-wound-surface areas of the dressing. Thus, the combination of adhesive and non-adhesive areas of the wound dressing provides the requisite pressure build-up to optimize fluid transfer through the slitted non-adhesive areas. The non-adhesive areas are preferably arranged in a uniform geometric pattern, e.g., in a series of rows covering the entire surface of at least that portion of the sheet material intended to cover the wound.

The vented wound dressing includes a thin conformable sheet material, at least a portion of which is adapted for placement as a dressing covering a wound. The portion for placement on a wound carries on one surface thereof a layer of a pressure-sensitive adhesive, the adhesive being applied to provide repeating areas containing no adhesive. At least a portion of the repeating areas of the sheet material contain no adhesive and may have slits extending through the thickness thereof to permit transfer of wound fluids through the sheet material unimpeded by the presence of adhesive material which can clog the slits and thereby inhibit fluid transfer therethrough.

The wound dressing preferably includes a continuous layer of adhesive around the periphery of the sheet material for securing the dressing to skin. This peripheral layer of adhesive maintains a barrier function against bacteria and other external contaminants. It also helps to insure that no wound fluids leak out of the dressing laterally.

The wound dressing also will include an absorbent layer adjacent the wound surface layer and in fluid communication with the non-adhesive wound surface layer for wicking wound fluids away from the wound surface. The absorbent layer will also be in fluid communication with the underside of the wound cover 18 such that suction within the wound cover 18 of the apparatus will pull fluid out of the wound dressing and into the bellows 12 via evacuation port 28 and inlet port 22.

With reference to FIGS. 2 and 3, a vented wound dressing 40 useful in the invention will comprise a thin conformable sheet material 42, at least a portion of which is adapted for placement over a wound. At least the portion adapted for placement over a wound has a pressure-sensitive adhesive layer 44 on one surface thereof, the adhesive layer being applied to provide repeating spaced areas 46 free of adhesive. Preferably the non-adhesive areas 46 are arranged in a geometric pattern, e.g., in staggered rows as shown in the drawing. In any case, while the non-adhesive areas 46 are shown for purposes of illustration as being generally circular, the configuration is not critical and they may conform to any desired shape, e.g., oval, rectangular, arcuate, etc.

Slits 48 are shown to be provided within each of the spaces defined by the non-adhesive areas. However, as heretofore stated, it is within the scope of this invention to provide slits in only a portion of the non-adhesive areas. While shown in FIGS. 2 and 5 to be somewhat arcuate in shape, slits 48 may have other forms.

As heretofore mentioned, the dressings useful in the invention contemplate a sheet material at least a portion of which is adapted for placement on a wound, that portion having the described adhesive layer and slits. For purposes of illustration, in the embodiment illustrated in FIG. 2, the entire surface area of the dressing is adapted to cover a wound and the adhesive and the non-adhesive areas with the slits accordingly extend to the edges of sheet material 42 defining the periphery of the dressing.

Wound dressings useful according to the invention will preferably also include an absorbent pad or other per se known equivalent fabric positioned on the non-adhesive bearing surface, i.e., above the dressing, to provide a reservoir for receiving and retaining wound exudate diffusing through the slits 48. Preferably, a cover sheet providing a bacterial barrier is situated over the fabric reservoir. Various materials and arrangements of elements providing this function are of course well known in the wound dressing art and consequently per se comprise no part of this invention.

However, another vented dressing useful in the invention is a modification of that described and claimed in Applicant's copending application, Ser. No. 461,598, filed Jan. 5, 1990. As disclosed therein, the wound dressing has a sealed absorbent fabric design and structure wherein an absorbent fabric providing a reservoir for retaining wound exudate is contained between a bottom liquid-permeable sheet material permitting the wicking or diffusion of wound exudate and an outer surface characterized as being a bacterial barrier, at least a portion of the outer surface also being air-permeable for permitting egress of air from the interstices or voids in the fabric reservoir to the ambient atmosphere. As stated therein, this removal or displacement of entrapped air within the fabric reservoir is necessary to free these interstices to act as a sponge for retention of wound fluid diffusing thereto, thereby appreciably increasing the capacity of the reservoir for receiving wound fluids. The modification of this wound dressing which renders the vented dressing useful according to this invention is replacement of the air-permeable portion of the outer surface with an air- and liquid-permeable portion, such that both air and fluid may exit the dressing via portions of the outer surface of the dressing.

Figure 4:
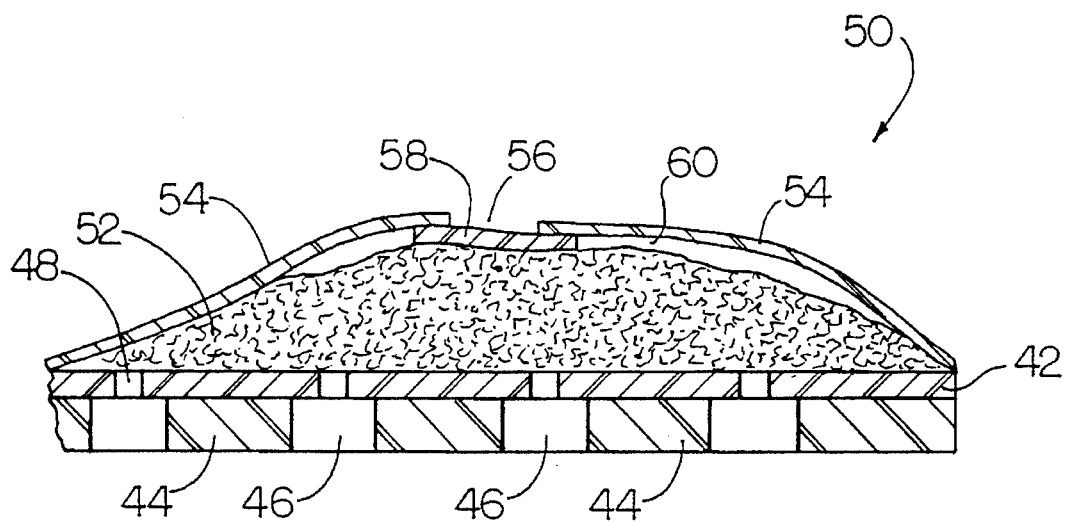
FIG. 4 is a fragmentary sectional view of another preferred embodiment of the wound dressing according to the invention.

FIG. 4 illustrates this embodiment of a wound dressing 50 useful according to the invention in which only portions of the non-wound surface side of the dressing, i.e., the outer surface, are fluid-permeable. This dressing is particularly useful for those embodiments of the invention in which the dressing is applied to the wound prior to positioning of the wound cover component of the exudate removal apparatus described herein. Thus, only limited portions of the dressing will be fully vented, or air- and fluid-permeable, allowing for increased protection of the vented dressing from contamination by ambient micro-organisms, as well as intermittent drainage of exudate contained in the dressing. The wound cover of the apparatus of the invention is positioned over the dressing. Upon application of suction through the wound over, the exudate is drawn from the wound dressing through the fluid-permeable portions of the outer surface of the dressing.

As shown in FIG. 4, an absorbent pad or other absorbent fabric 52 is seated on the surface of sheet 42 opposed from the adhesive-bearing surface. The absorbent fabric 52 is partially covered with a liquid-permeable and bacteria-impermeable outer sheet 54. Outer sheet 54 and sheet 42 are sealed in liquid- and bacteria-tight relationship around their common periphery so that exudate cannot escape through the edges of the dressing, nor can any external contaminants, including bacteria enter into the dressing and then pass through the slits 48 in sheet material 42 and then to the underlying wound.

The outer sheet 54 is provided with plural windows or openings 56 to permit egress of air and fluid from the interstices of the fabric reservoir 52 as well as the space 60 between the fabric 52 and outer sheet 54. Each such window or opening is shown to be covered by an air- and liquid-permeable sheet 58 of slightly larger dimensions than the dimensions of opening 56. Each sheet 58 also is sealed around its periphery to the edges of sheet 54 around opening 56.

The particular materials employed for preparing sheets 54, 58 and fabric 52 may be selected from those heretofore known in the art for providing their respective functions. Since such materials are well known and their selection will be a matter of choice within the expected judgement of the skilled worker in the light of the foregoing description, their selection per se accordingly comprises no part of this invention.

Liquid-impermeable sheet 54 should as stated be impermeable to bacteria as well. It may, for example, be on the order of 0.5 to 1.0 mil thick and comprise a suitable polymeric material such as polyurethane, "Saran" (trademark of Dow Chemical), a polyolefin such as polyethylene or polypropylene, a polyester such as polyethylene terephthalate, etc. In any event, sheet 54 should also be flexible and conformable.

Outer sheet 58 may comprise any of the per se known hydrophobic air-permeable filter, materials which are preferably impermeable to bacteria, e.g., per se known filter media in the 2–5 micron size.

Fabric 52 may comprise any of the fabric materials heretofore employed for wound dressings to retain exudate, e.g. cotton, gauze sponges, absorbent pads such as those customarily used for abdominal surgery, and the like. If desired, they may additionally contain an antimicrobial agent such as chlorhexidine, although the use of such a reagent is not considered necessary.

Referring again to FIGS. 2 and 3, the entire surface area of the dressing is adapted for placement over the wound and the slits (and adhesive/non-adhesive areas) extend to the edges of the dressing. However, the invention contemplates the use of wound dressings wherein only a portion of the sheet material constituting the dressing is intended to be placed on a wound.

Figure 5:
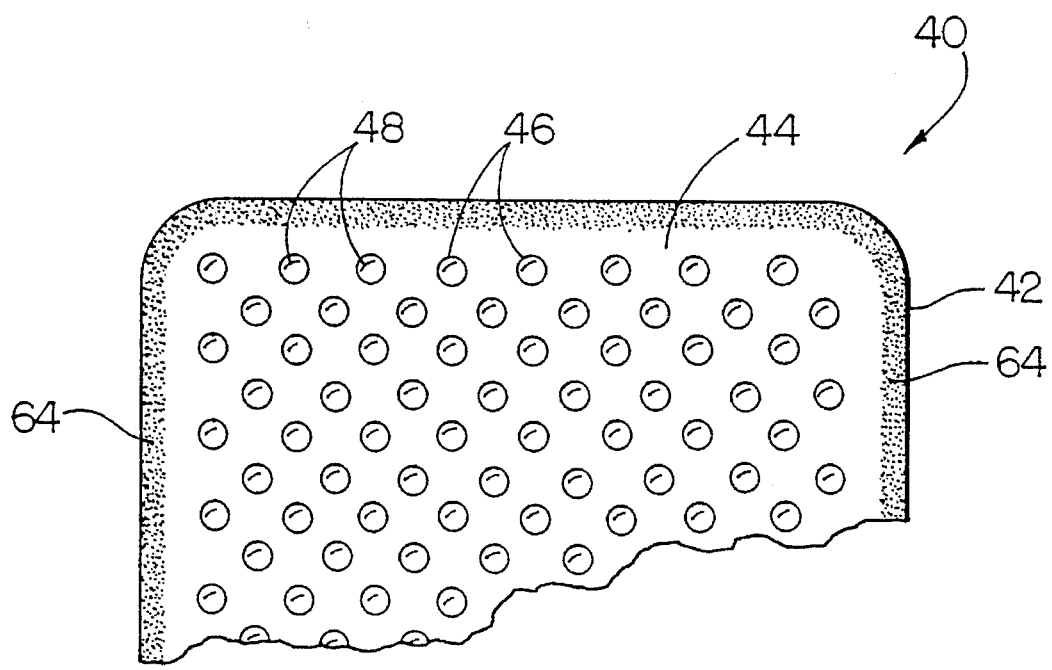
FIG. 5 is a fragmented plan view of a particularly preferred embodiment of the wound dressing according to the invention.

FIG. 5 is directed to a particularly preferred aspect of this invention embodying the latter concept.

As shown therein, a layer of pressure-sensitive adhesive 64 (which may be the same as or different from adhesive 44) is applied around the edges or periphery of sheet material 42, the adhesive 64 in turn defining the periphery of the portion of the dressing adapted for placement on the wound. Securing the dressing to the skin around its periphery in this manner serves to maintain the barrier function of the dressing against bacteria and other external contaminants as well as helping to insure that no wound exudate leaks out of the dressing laterally.

As heretofore mentioned, sheet 42 is flexible so as to be conformable to the contour of the body part to which it is to be applied. It may, for example, be as thin as 0.5 mil or as thick as 5.0 mil, but is preferably on the order of 1.0 mil thick. Preferably it is an elastomer which is characterized as being non-swellable or only slightly swellable. Materials useful for preparing slitted sheet 42 are well known in the art and will be readily suggested to those skilled in the art in the light of the foregoing description. By way of example, useful materials will include polyurethane, copolyesters such as 'HYTREL', polyvinyl chlorides, polyolefins, etc.

Wound cover 18 resembles sheet 42 in its flexibility, in that the wound cover must be substantially conformable to the wound dressing and thus the shape of the wound surface.

The adhesive materials employed for preparing layer 44 and the peripheral coating 64 (FIG. 5) may likewise be any of the known so-called medical grade or hypoallergenic adhesives heretofore employed in securing dressings to the skin. Such known adhesives include the rubber-based, acrylic, vinyl ether and hydrocolloid pressure-sensitive adhesives. The adhesives may be applied to provide a layer of at least 1 mil thick, but preferably layers of adhesive at least 5 mils thick, e.g. on the order of 5–10 mils, are contemplated.

In accordance with the preferred wound dressing, the adhesive-free areas containing the slits for transfer of wound exudate are isolated by adhesive coating forming a dam or barrier inhibiting lateral diffusion of the exudate so that it is instead directed upwardly through the slits provided in the dressing sheet, and then upward into the evacuation port 28 and ultimately into collection bag 20. For optimum effectiveness, the ratio of surface area of the portion of sheet 42 adapted for placement on the wound which contains adhesive to the surface area which does not should be at least 1:1, i.e. at least 50% of the surface area of that portion should contain adhesive.

The non-adhesive areas in theory need not be any larger than the slits to be provided therein. However, to provide optimum manufacturing tolerance for the slitting operation to be sure the slits do not at least in part inadvertently overlap into the adhesive area, the non-adhesive areas should be at least on the order of about ⅛ inch wide in the directions of the slit. For example, if the non-adhesive areas are circular, they should have a ⅛ inch diameter; and if they are square the length and width should be on the order of ⅛ inch. In any case, one skilled in the art will understand that the minimal dimensions will depend primarily upon the preciseness of the manufacturing equipment to provide the slits accurately in the prescribed non-adhesive areas.

In addition to permitting diffusion of wound exudate away from the wound and through the slits, it is essential that the wound dressings and the wound cover of the apparatus of the invention provide a barrier to evaporation of water (as distinguished from a barrier to removal of exudate) so as to keep the wound surface moist as excess exudate is removed. The benefits of maintaining a moist wound surface are well-known, and include faster re-epithelialization, less pain and better cosmetic results.

The size and number of slits in the dressing should be such as to provide a dressing of the type known in the art as a moist healing wound dressing. The size and number of slits also should be such as to maintain a moisture vapor permeability or transition rate for the dressing of no greater than 1500 grams/meter/24 hours at 37° C. and 50% relative humidity.

The slits will optimally extend across the width or diameter of the non-adhesive areas. With ⅛" diameter circular areas, excellent results have been obtained with cross slits across the diameter of the circle. Many other slit designs may also be employed. For example, equal success has been obtained with 3/64 inch radius half circle slits in ⅛ inch diameter circles as well as S-shaped slits in ¼ inch diameter areas.

The above-described wound dressing useful according to the invention may be prepared as follows. First, an adhesive layer of the desired thickness by is applied, e.g., by calendaring, casting, etc. between two release sheets of differential affinity; second, holes of the desired configuration and spacing are punched through the thickness of the resulting "sandwich"; third, a release sheet of lesser affinity is removed from the adhesive, leaving another release sheet of greater affinity adhering to the opposed surface of the adhesive; fourth, the free adhesive surface is applied to the surface of the desired elastomeric sheet; fifth, slits are provided by cutting the sheet in areas where there is no adhesive, i.e. in those areas where holes had been punched through the adhesive "sandwich"; and sixth, the release sheet having the holes punched through it are replaced with a new one free from holes, if desired.

The further steps required to provide dressings such as shown in FIGS. 4 and 5 will be readily apparent to those skilled in the art and need not be discussed in further detail.

In operation, the wound evacuation apparatus is used as follows. The apparatus is affixed to the patient's bed or clothing at a position below the wound site. The wound cover 18, including wound dressing 40, is placed over the wound for a time sufficient to allow wound exudate to be absorbed into the wound dressing. Where the wound dressing 40 is applied separately to the wound site, the wound cover 18 is subsequently placed over the dressing. FIG. 1 depicts the apparatus before manual drainage, with bellows 12 extended. To initiate drainage, the bellows may be manually compressed, forcing the air in the bellows through outlet port 16 and into collection bag 20. The resilient bellows 12 are then permitted to expand. Because the system is closed, liquid and gases are drawn from the wound site through the evacuation port 28, past one-way valve 22 in inlet port 14, and into bellows 12. Once started, the bellows continue filling with fluid until the fluid reaches the bellows top. Due to the siphoning effected produced by the positioning of the apparatus below the wound site, surplus liquid automatically enters collection bag 20 via outlet port 16 and one-way valve 24. The fluid entering the bag displaces any gases therein, which exit the bag via the vent 32.

In order to force all of the fluid contained in bellows 12 into collection bag 20, the bellows is again compressed such that the remaining fluid contained in bellows 12 is forced out. Due to the presence of the one-way valve, fluid can only exit bellows 12 via one-way valve 24 in outlet port 16.

The compressed bellows are allowed to expand again, thus drawing more wound exudate out of the wound dressing and wound site. The bellows compression/expansion process is repeated until the collection bag is filled, whereupon the entire suctioning device is removed from the wound dressing and disposed of. Alternatively, suction may be accomplished by an automated system, the details for which are known to those of skill in the art, and are not per se part of the invention.

OTHER EMBODIMENTS

Other embodiments will be evident to those of skill in the art. It should be understood that the foregoing detailed description is provided for clarity only and is merely exemplary. The spirit and scope of the present invention are not limited thereto, being defined by the claims set forth below.

I claim:

1. An apparatus for evacuation of exudate from wounds, comprising a suctioning means having an inlet port and an outlet port;

a wound cover in fluid communication with said suctioning means via said inlet port, said wound cover being adapted to fit in fluid communication with a wound dressing for application to a wound site; and a vented wound dressing comprising a thin conformable sheet material at least a portion of the surface area of which is intended for placement as a dressing over a wound, which portion carries a pressure-sensitive adhesive coating on one surface thereof for adhering the dressing to skin, the coating being applied to provide repeating areas of the sheet material containing no adhesive, at least a portion of the repeating areas of no adhesive having slits extending through the thickness thereof to permit transfer of wound fluids through the sheet material unimpeded by presence of adhesive material which can clog the slits and thereby inhibit fluid transfer therethrough.

2. The apparatus of claim 1, further comprising a collection bag in fluid communication with said suctioning means via said outlet port.

3. The apparatus of claim 1, said suctioning means being compressible and expandable.

4. The apparatus of claim 1, said inlet port being fitted with a one-way inlet valve and said outlet port being fitted with a one-way outlet valve.

\* \* \* \* \*